United States Patent
Hähnle et al.

(10) Patent No.: US 6,245,410 B1
(45) Date of Patent: Jun. 12, 2001

(54) ABSORBER ELEMENT OF SUPERABSORBENT FOAMS HAVING ANISOTROPIC SWELLING BEHAVIOR

(75) Inventors: Hans-Joachim Hähnle, Neustadt; Manfred Walter, Speyer; Jürgen Tropsch, Römerberg; Jens Kremeskötter, Ludwigshafen; Gunnar Schornick, Neuleiningen; Thomas Anstock, Weisenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/117,287

(22) PCT Filed: Feb. 27, 1997

(86) PCT No.: PCT/EP97/00963

§ 371 Date: Aug. 25, 1998

§ 102(e) Date: Aug. 25, 1998

(87) PCT Pub. No.: WO97/31600

PCT Pub. Date: Sep. 4, 1997

(30) Foreign Application Priority Data

Feb. 28, 1996 (DE) .............................. 196 07 529

(51) Int. Cl.$^7$ .............................. A61F 13/15; A61L 15/42; A61L 15/60

(52) U.S. Cl. .................. 428/132; 428/134; 428/158; 428/316.6; 428/913; 442/370

(58) Field of Search ................ 156/77, 78; 428/67, 428/132, 133, 134, 158, 173, 316.6, 913; 442/370

(56) References Cited

U.S. PATENT DOCUMENTS

| | | |
|---|---|---|
| 4,235,237 * | 11/1980 | Mesek et al. .................. 128/284 |
| 4,394,930 | 7/1983 | Korpman . |
| 4,415,388 | 11/1983 | Korpman . |
| 4,529,739 | 7/1985 | Scott et al. . |
| 4,649,154 | 3/1987 | Dolman et al. . |
| 4,725,628 | 2/1988 | Garvey et al. . |
| 4,725,629 | 2/1988 | Garvey et al. . |
| 4,731,391 | 3/1988 | Garvey . |
| 4,806,408 * | 2/1989 | Pierre et al. ............................ 428/76 |
| 4,808,637 | 2/1989 | Boardman et al. . |
| 4,990,541 | 2/1991 | Nielsen et al. . |
| 5,175,046 * | 12/1992 | Nguyen ................................ 428/198 |
| 5,182,312 | 1/1993 | Engelhardt et al. . |
| 5,338,766 * | 8/1994 | Phan et al. ............................ 521/63 |
| 5,763,067 * | 6/1998 | Brüggemann et al. .......... 428/317.9 |

FOREIGN PATENT DOCUMENTS

| | | |
|---|---|---|
| 195 409 51 | 11/1995 | (DE) . |
| 0 421 264 | 4/1991 | (EP) . |
| 0 427 219 | 5/1991 | (EP) . |
| 2 136 813 | 9/1984 | (GB) . |
| WO 88/09801 | 12/1988 | (WO) . |
| WO 93/04092 | 3/1993 | (WO) . |
| WO 94/07935 | 4/1994 | (WO) . |
| WO 94/22502 | 10/1994 | (WO) . |

OTHER PUBLICATIONS

R.Y. Lochhead, et al., Polymers & Thickeners, Cosmetics and Toiletries, vol. 108, pp. 95–135, "Encyclopedia of Polymers and Thickeners for Cosmetics", May 1993.

M.T. Clarke, Rheological Properties of Cosmetics and Toiletries, Cosmetic Science and Technology Series, vol. 13, pp. 55–152, "Rheological Additives", 1993 (Month unknown).

* cited by examiner

Primary Examiner—Blaine Copenheaver
(74) Attorney, Agent, or Firm—Oblon, Spivak, McClelland, Maier & Neustadt, P.C.

(57) ABSTRACT

Absorber elements are described of at least one composite material having absorbent elements on a support, in which a plurality of elements of a superabsorbent foam are arranged on at least one support in a grid pattern at distances such that the elements in the swollen state touch at their peripheries.

15 Claims, 3 Drawing Sheets

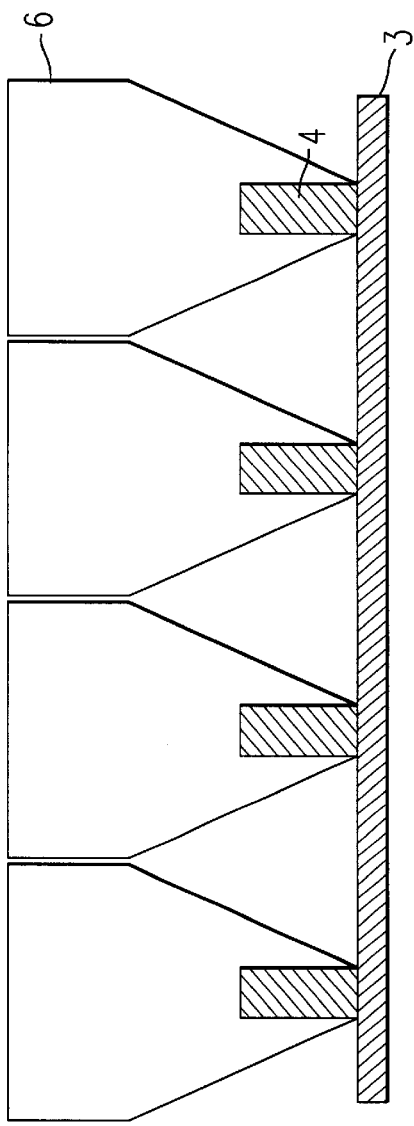
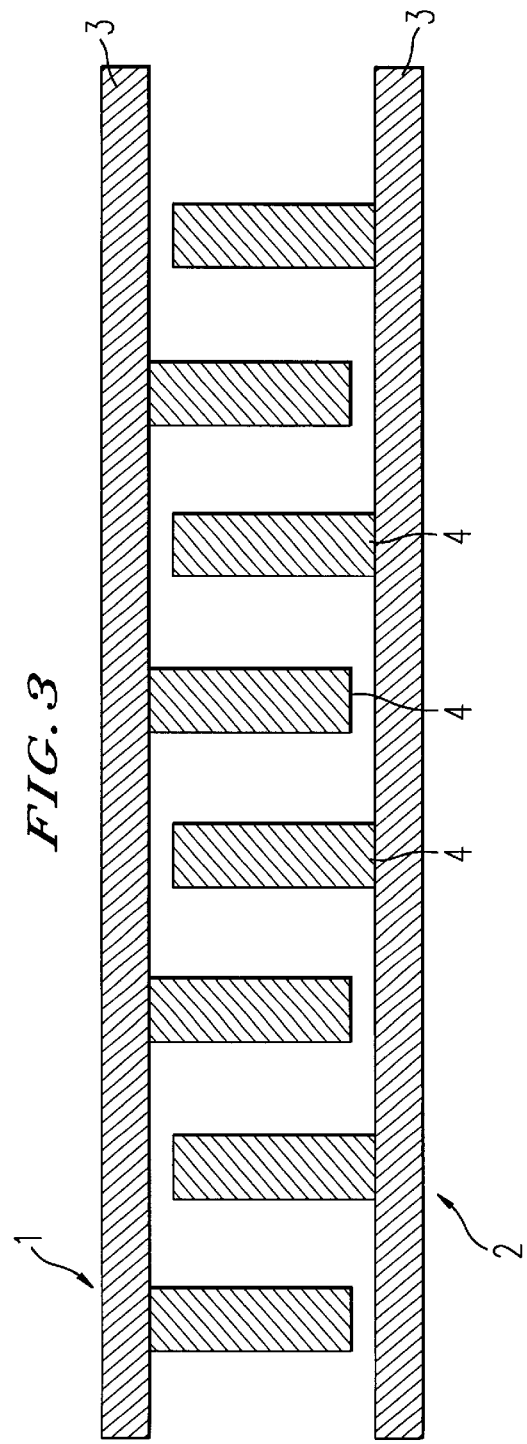

ABSORBER ELEMENT OF SUPERABSORBENT FOAMS HAVING ANISOTROPIC SWELLING BEHAVIOR

The present invention relates to absorber elements having anisotropic swelling behavior made of at least one composite material having absorbent elements on a support, and to their production and use.

Water-absorbent foamed crosslinked polymers, which are frequently termed superabsorbent polymers or foams or superabsorbents, are able to absorb many times their own weight of aqueous liquids, forming hydrogels. These polymers are therefore used, for example, in hygiene products, such as diapers, for absorbing urine. They have the property of retaining the absorbed liquid even under mechanical load.

The polymers mentioned are frequently employed in hygiene or sanitary products in the form of composite materials. Thus, WO-A-88/09801 describes a water-swellable polymeric absorption material, which can be used in the form of a laminate with a woven fabric. WO-A-94/07935 describes water-absorbent hydrophilic polyurethane gel foams which can be applied to sheet supports, such as woven fabrics, knitted fabrics, webs or films.

EP-A-427 219 and U.S. Pat. No. 4,990,541 disclose water-absorbent latex foams into which superabsorbent finely divided materials can be incorporated after the foaming process.

WO-A-94/22502 describes a superabsorbent polymer foam which can be employed for producing hygiene articles, such as diapers. For this purpose, the polymer foam is applied to a support, with the polymer foam being able to cover the surface of the support in part or completely and being able to be applied in any desired pattern, with the pattern being formed from relatively large joined surfaces of the polymer foam and having the purpose of distributing the absorbent areas of the hygiene article in the desired manner.

The superabsorbent polymers have the property of expanding essentially isotropically in all three directions in space when aqueous liquids are absorbed. Generally, the polymers expand in each direction by a factor of from 2 to 5, so that a total increase in volume of a factor from 8 to 125 may be observed. In practice, it has been found that this property is disadvantageous in the construction of hygiene articles, since an area expansion of the polymers over a relatively large range is generally impossible. In addition, consideration must be given to the fact that, with an area expansion by a factor of from 4 to 25, when a single foam layer is placed into a diaper, only between ¼ or 1/25 of the diaper surface may be covered by the foam, in order to have enough room for the swelling. This means that effective absorption of the body fluids which are released is not ensured in every case in this manner, so that complete absorption, for example in the case of diapers, must be ensured in other ways. If, in contrast, all of the available area in a diaper is covered with a superabsorbent polymer layer, as mentioned, there is insufficient space available to enable effective and rapid swelling of the polymer layer and thus effective absorption of the body fluids.

Attempts to solve these problems by producing simple composite materials, as described in the prior art, have failed. Regardless of whether a foam layer is applied to a support, a foam layer is introduced between two supports or a composite is provided in which a support material is embedded in the foam, disintegration of the composite materials during the swelling process is always observed. The composite materials sometimes delaminate at the support/polymer layer interface, but more frequently it is observed that cracks form within the partially swollen polymer layers and thus extensive polymer pieces detach from the composite material. After breakdown of the composite, the detached polymer particles swell unhindered isotropically in all three spatial directions. It is an object of the present invention, therefore, to provide an absorber element which is based on a composite material of a support and a water-absorbent polymer foam and is able to absorb liquids effectively and rapidly without the composite breaking down during the swelling process.

We have found that this object is achieved, surprisingly, by an absorber element which expands essentially in only one dimension, that is perpendicularly to the support material.

The present invention therefore relates to an absorber element of at least one composite material having absorbent elements on a support in which a plurality of elements of a superabsorbent foam (foam elements) are arranged on at least one support in a grid pattern at distances in such a manner that the elements in the swollen state touch at their peripheries.

The grid pattern can be chosen without restriction. However, care must be taken to ensure that the individual foam elements are spaced from one another in a manner such that sufficient space is available to enable complete swelling of the foam elements. The distance between the foam elements is preferably selected in a manner such that they are in contact with one another after the swelling process is complete. If the isotropic swelling factor is 3.0, for example, the distance between the foam elements must—in the case of cylindrical foam elements—correspond to twice the diameter of the cylinders. Therefore, an open area 8 times that of the original foam element must be available in a ring shape around the original foam element.

However, it can also be advantageous to choose the distances between the foam elements to be up to 50%, in particular up to 20%, less than the distance required for the foam elements just to touch in the swollen state. An additional stability of the swollen composite material can be achieved in this manner.

However, on the other hand, it can also be advantageous to choose the distances to be up to 100%, preferably up to 50%, greater than the distance required for the foam elements to touch one another in the swollen state. Composite materials are obtained in this manner which, even in the swollen state, have a permeability to incident liquids.

By applying the polymer foams in the form of a grid in the manner described, the composite material essentially expands anisotropically, that is it expands significantly only in a direction perpendicular to the support material. Expansion of the composite material in the direction parallel to the surface of the support material, in contrast, essentially does not occur.

The shape of the foam elements can generally be chosen without restriction. They generally represent elevations on the support, which may be cylindrical, hemispherical, pyramidal, conical, truncated pyramidal, truncated conical, etc. If an increased permeability of the composite material is desired, the shape of the foam elements is chosen in a manner such that gaps (gusset volumes) remain between the swollen foam elements which ensure a high vertical permeability. This is preferably achieved by employing foam elements in the form of cylinders or cylindrical elevations or elevations having pentagonal cross-section.

If, in contrast, a composite material is desired in which the swollen foam elements form an essentially closed surface, i.e. the foam elements cover the surface, as foam elements, use is preferably made of elevations having triangular, square, rectangular or hexagonal cross-section.

Preference is given to foam elements having hexagonal or circular cross-section.

The flank angle of the foam elements, i.e. the angle between the support surface and the lateral surface of the foam element, can be chosen without restriction. Expediently, it is 90°. However, in some cases it is advantageous if the angle is smaller, preferably in the range 20–90°, and in particular in the range 50–90°. Foam elements are then present in the shape of a cone or a pyramid or in the shape of a truncated cone or a truncated pyramid.

The height of the foam elements depends on the application of the absorber element. For hygiene and sanitary articles it is generally in the range from about 0.1 mm to about 20 mm. The cross-sectional area of the foam elements is generally in the range from 1 to 400 mm$^2$, preferably from 2 to 100 mm$^2$. The ratio of height (in mm) to cross-sectional area of the foam elements (in mm$^2$) is preferably in the range from 10 to 0.01, in particular in the range from 5 to 0.01.

The absorber element of the invention can include one or more composite materials. If it includes a plurality of composite materials, these can be made up in the manner of a sandwich, in which a structured foam layer is incorporated between two identical or different support materials. However, multilayer sandwich composite materials are also possible.

According to a preferred embodiment, the absorber element of the invention includes two composite materials which lie opposite one another by the sides bearing the foam elements in a manner such that the foam elements of the one composite material penetrate into the spaces between the foam elements of the other composite material. Generally, it is sufficient to join the two composite materials in the manner described. In some circumstances, to improve stability, it can also be useful to fix the two composite materials to one another with a water-soluble glue. An absorber element of this type has the advantage that the absorption capacity per unit volume is considerably increased. It is particularly expedient in this case to employ foam elements for which the flank angle is <90°, as defined above.

Furthermore, in the case of this embodiment it is also possible that one composite material has foam elements which show a closed surface in the swollen state, whereas the other composite material has foam elements between which gaps remain in the swollen state. This enables effective transport of liquids vertically through the second composite material.

Support materials which are suitable are in principle all materials which are usable in the production of hygiene or sanitary articles. They can be liquid-permeable or -impermeable. Preference is given to the following materials:

a) polymer films or metal foils, in particular backing sheet materials such as polyethylene and polypropylene;

b) nonwovens of synthetic and/or semisynthetic and/or natural fibers having a weight per unit area of 5–400 g/m$^2$, which can be made with known production methods. These include, e.g., spunbonded, thermobonded, melt-blown, air-laid, through air bonded and needle stitched fibers. An extensive compilation of the production of nonwovens may be found in Nonwovens Industry, 1992, 37–41 and 1996, 94–95. Combinations with various materials, e.g. polyesters and polyolefins, or of various fiber types of a material, may also be employed. In addition, composites of nonwovens which are produced by diverse processes mentioned above are also suitable.

The nonwovens used can be made permanently or semi-permanently hydrophilic by suitable methods, c) papers, as are used, e.g., as handkerchieves or hand towels;

d) woven fabrics of synthetic or nonsynthetic fibers e) other foams

Those which are especially of interest here are open-cell foams which are hydrophilic or can be made hydrophilic and, furthermore, are still soft and flexible.

Suitable superabsorbent foams are all known hydrophilic foams which have a minimum absorption capacity of 10 ml of synthetic urine per gram of dry foam and have an absorption speed of at least 0.1 g of synthetic urine per gram of foam and second. Examples are the following foams, which are described in the patents and patent applications also listed, the contents of which are herewith incorporated by reference.

| | |
|---|---|
| SAP in PU foam | US-A-4,725,628, US-A-4,725,629, US-A-4,731,391 |
| PU foam with SAP as interpenetrating network | EP-A-427219 US-A-4,990,541 |
| Extruded SAP foam | US-A-4,394,930, US-A-4,415,388, GB-A-2 136813 |
| $CO_2$-blown SAP foam | US-A-4,529,739 US-A-4,649,154 |
| SAP foam, water-insoluble blowing agent | WO-A-94/22502 |
| SAP foam from O/W emulsion | EP-A-0 421 264 |
| SAP foam with blowing agent from polymers | WO-A-88/09801 |
| $CO_2$-blown monomer mixture | EP-A-2 954 438 US-A-4,808,637 |
| post-crosslinked SAP foam | WO-A-93/04092 |
| (SAP = superabsorbent polymer). | |

Preferably, however, a water-absorbent crosslinked polymer foam is employed which is obtainable by (I) foaming a polymerizable aqueous mixture which consists of (a) monoethylenically unsaturated monomers containing acid groups, which are at least 50 mol % neutralized, (b) with or without other monoethylenically unsaturated monomers, (c) crosslinkers, (d) initiators, (e) from 0.1 to 20% by weight of at least one surfactant, (f) with or without one or more solubilizer and (g) with or without thickeners, foam stabilizers, polymerization regulators, fillers and/or cell nucleating agents, the foaming being performed by dispersing fine bubbles of a gas inert to free-radicals, and (II) polymerizing the foamed mixture forming a foamed hydrogel and setting the water content of the foamed polymer to from 1 to 45% by weight.

A polymerizable aqueous mixture is processed to form a foam which is stable to processing and can be shaped as required. The polymerizable aqueous mixture includes as component (a) mono-ethylenically unsaturated monomers which contain acid groups, which are at least 50 mol % neutralized. Examples of such monomers are monoethylenically unsaturated $C_3$–$C_{25}$-carboxylic acids or anhydrides, for example acrylic, methacrylic, ethacrylic, α-chloroacrylic, crotonic and maleic acids, maleic anhydride, itaconic, citraconic, mesaconic, glutaconic, aconitic and fumaric acids.

In addition, monoethylenically unsaturated sulfonic acids can be used as monomers of the group (a), for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, vinylphosphoric acid, allylphosphonic acid and 2-acrylamido-2-methylpropanesulfonic acid. The monomers can be used alone or in a mixture in the preparation of the superabsorbent foams. Preferred monomers of the group (a) used are acrylic, methacrylic, vinylsulfonic, acrylamidopropanesulfonic acid or mixtures of these, eg. mixtures of acrylic and methacrylic acid, mixtures of acrylic and acrylamidopropanesulfonic acid or mixtures of acrylic and vinylsulfonic acid.

The monomers are at least 50 mol % neutralized with, for example, alkali metal bases or ammonia or amines. Preferably, sodium hydroxide solution or potassium hydroxide solution is used for neutralization. However, the neutralization can also be carried out using sodium carbonate, sodium hydrogencarbonate, potassium carbonate or potassium hydrogencarbonate or other carbonates or hydrogencarbonates or ammonia. The acid groups of the monomers are preferably at least 65 mol % neutralized.

The polymerizable aqueous mixture may contain monomers of the group (b). For the purposes of the invention these are taken to mean other monoethylenically unsaturated monomers which can be copolymerized with the monomers (a) and (c). These include, for example, $C_2$–$C_{25}$-olefins, the amides and nitriles of monoethylenically unsaturated carboxylic acids, eg. acrylamide, methacrylamide and N-vinylformamide, acrylonitrile and methacrylonitrile, dialkyldiallylammonium halides, such as dimethyldiallylammonium chloride, diethyldiallylammonium chloride, allylpiperidinium bromide, N-vinylimidazoles, such as N-vinylimidazole, 1-vinyl-2-methylimidazole, and N-vinylimidazolines, such as N-vinylimidazoline, 1-vinyl-2-methylimidazoline, 1-vinyl-2-ethylimidazoline or 1-vinyl-2-propylimidazoline, which can be used in the polymerization in the form of the free bases, in quaternized form or as salt. Other compounds which are suitable are dialkylaminoalkyl acrylates and dialkylaminoalkyl methacrylates, dimethylaminoethyl acrylate, dimethylaminoethyl methacrylate, diethylaminoethyl acrylate and diethylaminoethyl methacrylate. The basic esters are preferably used in quaternized form or as salt. Further suitable compounds of the group (b) are, for example, vinyl esters of saturated $C_1$–$C_4$-carboxylic acids, such as vinyl formate, vinyl acetate or vinyl propionate, alkyl vinyl ethers having at least 2 carbon atoms in the alkyl group, such as ethyl vinyl ether or butyl vinyl ether, esters of monoethylenically unsaturated $C_3$–$C_6$-carboxylic acids, eg. esters of mono-hydroxy $C_1$–$C_{18}$-alcohols and acrylic acid, methacrylic acid or maleic acid, half-esters of maleic acid, eg. monomethyl maleate, and hydroxyalkyl esters of said monoethylenically unsaturated carboxylic acids, eg. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams, such as N-vinylpyrrolidone or N-vinylcaprolactam, acrylic and methacrylic esters of alkoxylated monohydric saturated alcohols, eg. of alcohols having from 10 to 25 carbons which have been reacted with from 2 to 200 mol of ethylene oxide and/or propylene oxide per mole of alcohol, and monoacrylic esters and monomethacrylic esters of poly (ethylene glycol) or poly(propylene glycol), where the molar masses ($M_N$) of the polyalkylene glycols can be up to 2000, for example. Other monomers of the group (b) which are suitable are alkyl-substituted styrenes, such as ethylstyrene or tert-butyl styrene. The monomers of the group (b) can also be used in a mixture in the copolymerization with the other monomers, eg. mixtures of vinyl acetate and 2-hydroxyethyl acrylate in any ratio.

The monomers of the group (c) have at least 2 ethylenically unsaturated double bonds. Examples of monomers of this type, which are conventionally used as crosslinkers in polymerization reactions, are N,N'-methylenebisacrylamide, polyethylene glycol diacrylates and polyethylene glycol dimethacrylates, which are each derived from polyethylene glycols of a molecular weight of from 106 to 8500, preferably from 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, diesterified or triesterified, with acrylic or methacrylic acid, polyhydric alcohols, such as glycerol or pentaerythritol, triallylamine, tetraallylethylenediamine, divinylbenzene, diallyl phthalate, polyethylene glycol divinyl ethers of polyethylene glycols of a molecular weight of from 126 to 4000, trimethylolpropane diallyl ether, butanediol divinyl ether, pentaerythritol triallyl ether and/or divinylethyleneurea. Preferably, water-soluble crosslinkers are used, eg. N,N'-methylenebisacrylamide, polyethylene glycol diacrylates and polyethylene glycol dimethacrylates, which are derived from addition products of from 2 to 400 mol of ethylene oxide to 1 mol of a diol or polyol, vinyl ethers of addition products of from 2 to 400 mol of ethylene oxide to 1 mol of a diol or polyol, ethylene glycol diacrylate, ethylene glycol dimethacrylate or triacrylates and trimethacrylates of addition products of from 6 to 20 mol of ethylene oxide to one mol of glycerol, pentaerythritol triallyl ether and/or divinylurea.

In addition, compounds can be used as crosslinkers which contain at least one polymerizable ethylenically unsaturated group and at least one further functional group. The functional group of these crosslinkers must be able to react with the functional groups of the monomers (a), essentially the carboxyl groups or sulfonic acid groups. Examples of suitable functional groups are hydroxyl, amino, epoxy and aziridino groups.

In addition, compounds can be used as crosslinkers which bear at least two functional groups which can react with the carboxyl and sulfonic acid groups of the group (a) monomers used. The suitable functional groups have already been mentioned above, ie. hydroxyl, amino, epoxy, isocyanate, ester, amide and aziridino groups. Examples of crosslinkers of this type are ethylene glycol, diethylene glycol, triethylene glycol, tetraethylene glycol, polyethylene glycol, glycerol, polyglycerol, propylene glycol, diethanolamine, triethanolamine, poly(propylene glycol), block copolymers of ethylene oxide and propylene oxide, sorbitan fatty esters, ethoxylated sorbitan fatty esters, trimethylolpropane, pentaerythritol, poly(vinyl alcohol), sorbitol, poly(glycidyl ethers), such as ethylene glycol diglycidyl ether, poly (ethylene glycol) diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and poly(propylene glycol) diglycidyl ether, polyaziridine compounds, such as 2,2-bishydroxymethylbutanol tris[3-(1-aziridinyl)propionate], 1,6-hexamethylenediethyleneurea, diphenylmethane-bis-4, 4'-N,N'-diethyleneurea, haloepoxy compounds, such as epichlorohydrin and α-methylfluorohydrin, polyisocyanates, such as 2,4-toluylene diisocyanate and hexamethylene diisocyanate, alkylenecarbonates, such as 1,3-dioxolan-2-one and 4-methyl-1,3-dioxolan-2-one, polyquaternary amines, such as condensation products of dimethylamine with epichlorohydrin, homo- and copolymers of diallyldimethylammonium chloride and homo- and copolymers of dimethylaminoethyl (meth)acrylate, which may be quaternized with methyl chloride, for example.

Other suitable crosslinkers are polyvalent metal ions which are able to form ionic crosslinks. Examples of crosslinkers of this type are magnesium, calcium, barium and aluminum ions. These crosslinkers are added to the aqueous polymerizable solution as hydroxides, carbonates or hydrogencarbonates, for example.

Other suitable crosslinkers are multifunctional bases which are likewise able to form ionic crosslinks, for example polyamines or their quaternized salts. Examples of polyamines are ethylenediamine, diethylenetriamine, triethylenetetraamine, tetraethylenepentamine, pentaethylenehexamine and polyethyleneimines and polyvinylamines having molar masses in each case of up to 4,000,000.

In a preferred embodiment of the invention, two different crosslinkers are used, of which one is water-soluble and the other water-insoluble. The hydrophilic crosslinker, which is soluble in the aqueous phase of the reaction mixture, causes in a conventional manner a relatively uniform crosslinking of the resulting polymer, as is customary in the preparation of a superabsorbent. The hydrophobic crosslinker, which is insoluble, or only sparingly soluble, in the polymerizable aqueous mixture, accumulates in the surfactant boundary layer between the gas phase and the polymerizable aqueous phase. As a result, in the subsequent polymerization, the surface of the foam is more extensively crosslinked than the inner part of the superabsorbent hydrogel. A core-shell foam structure is thus obtained directly in the preparation of the superabsorbent foam. An extensive surface crosslinking of this type in a superabsorbent foam is only possible in the known prior art preparation processes by subsequent crosslinking on the surface of a previously formed foamed superabsorbent. For this post-crosslinking, in the conventional procedure, a separate process step is necessary, which can be omitted in the process of the present invention.

Products according to the invention having a core-shell structure exhibit markedly improved properties in comparison with homogenerously crosslinked samples with respect to the absorption rate, distribution action and gel stability. With the exception of polyvalent metal ions, all of the above described water-insoluble crosslinkers which can be assigned to the different groups are suitable for preparing foams having a core-shell structure, ie. foams in which the entire surface is more extensively crosslinked than the underlying layer, which has been termed the core layer above. Particularly preferred hydrophobic crosslinkers are diacrylates or dimethacrylates or divinyl ethers or alkanediols having from 2 to 25 carbons (branched, linear, with any arrangement of the OH groups), such as 1,3-propanediol, 1,4-butanediol, 1,6-hexanediol, neopentyl glycol, 1,9-nonanediol or 1,2-dodecanediol, di- or tripropylene glycol diacrylates or dimethacrylates, polypropylene glycol diacrylates or dimethacrylates, allyl acrylate, allyl methacrylate, divinylbenzene, glycidyl acrylate or glycidyl methacrylate, allyl glycidyl ethers and bisglycidyl ethers of the above listed alkanediols.

Suitable hydrophilic crosslinkers are, for example, N'-methylenebisacrylamide, polyethylene glycol diacrylates or dimethacrylates having a molecular weight $M_N$ of from 200 to 4000, divinylurea, triallylamine, diacrylates or dimethacrylates of addition products of from 2 to 400 mol of ethylene oxide to 1 mol of a diol or polyol or the triacrylate of an addition product of 20 mol of ethylene oxide to 1 mol of glycerol, and vinyl ethers of addition products of from 2 to 400 mol of ethylene oxide to 1 mol of diol or polyol.

The monomers of the group (a) are present in the polymerizable aqueous solution, for example, in amounts of from 10 to 80, and preferably from 20 to 60, % by weight. The monomers of the group (b) are only used if appropriate for modifying the superabsorbent foams and can be present in the polymerizable aqueous mixture in amounts of up to 50, preferably in amounts of up to 20, % by weight. The crosslinkers (c) are present in the reaction mixture, for example, from 0.001 to 5, and preferably from 0.01 to 2, % by weight.

Polymerization initiators which can be used are all initiators forming free-radicals under the polymerization conditions which are customarily used in the preparation of superabsorbents. Initiation of polymerization by the action of electron beams on the polymerizable aqueous mixture is also possible. However, the polymerization can also be initiated in the absence of initiators of the abovementioned type by the action of high-energy radiation in the presence of photoinitiators.

Polymerization initiators which can be used are all compounds decomposing into free radicals under the polymerization conditions, eg. peroxides, hydroperoxides, hydrogen peroxide, persulfates, azo compounds and redox catalysts. Preference is given to the use of water-soluble initiators. In some cases it is advantageous to use mixtures of different polymerization initiators, eg. mixtures of hydrogen peroxide and sodium peroxodisulfate or potassium peroxodisulfate, mixtures of hydrogen peroxide and sodium peroxodisulfate can be used in any ratio. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butylpermaleate, tert-butyl perbenzoate, di-(2-ethylhexyl) peroxodicarbonate, dicyclohexyl peroxodicarbonate, di-(4-tert-butyl-cyclohexyl) peroxodicarbonate, dimyristyl peroxodicarbonate, diacetyl peroxodicarbonate, allyl peresters, cumyl peroxyneodecanoate, tert-butyl per-3,5,5-trimethylhexanoate, acetyl cyclohexylsulfonyl peroxide, dilauryl peroxide, dibenzoyl peroxide and tert-amyl perneodecanoate. Particularly suitable polymerization initiators are water-soluble azo starters, eg. 2,2'-azobis-(2-amidinopropane) dihydrochloride, 2,2'-azobis-(N,N'-dimethylene)isobutyramidine dihydrochloride, 2-(carbamoylazo)isobutyronitrile, 2,2'-azobis[2-(2'-imidazolin-2-yl)propane] dihydrochloride and 4,4'-azobis-(4-cyanovaleric acid). Said polymerization initiators are used in customary amounts, eg. in amounts of from 0.01 to 5, preferably from 0.1 to 2.0, % by weight, based on the monomers to be polymerized.

Suitable initiators are, in addition, redox catalysts. The redox catalysts include as oxidizing component at least one of the abovementioned per compounds and, as reducing component, for example, ascorbic acid, glucose, sorbose, ammonium or alkali metal hydrogen sulfite, ammonium or alkali metal sulfite, ammonium or alkali metal thiosulfate, ammonium or alkali metal hyposulfite, ammonium or alkali metal pyrosulfite or ammonium or alkali metal sulfide, metal salts, such as iron(II) ions or silver ions or sodium hydroxymethylsulfoxylate. Preferably, ascorbic acid or sodium sulfite is used as the reducing component of the redox catalyst. Based on the amount of monomer used in the polymerization, for example, from $3 \cdot 10^{-6}$ to 1 mol % of the reducing component of the redox catalyst system is used, and from 0.001 to 5.0 mol % of the oxidizing component.

If the polymerization is triggered by the action of high-energy radiation, as initiator use is customarily made of photoinitiators. These can be, for example, α-cleavage compounds, H-abstracting systems or else azides. Examples of such initiators are benzophenone derivatives, such as Michler's ketone, phenanthrene derivatives, fluorene derivatives, anthraquinone derivatives, thioxanthone derivatives, coumarin derivatives, benzoin ethers and their derivatives, azo compounds such as the free-radical formers mentioned above, substituted hexaarylbis-imidazoles or acylphosphine oxides. Examples of azides are: 2-(N,N-dimethylamino)-ethyl 4-azidocinnamate, 2-(N,N-dimethylamino)-ethyl 4-azidonaphthyl ketone, 2-(N,N-dimethylamino)-ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis (p-azidobenzylidene)-4-methyl-cyclohexanone. The photoinitiators, if used, are customarily employed in amounts of from 0.01 to 5% by weight, based on the monomers to be polymerized.

The polymerizable aqueous mixtures contain as component (e) from 0.1 to 20% by weight of at least one surfactant. The surfactants are of critical importance for the preparation and stabilization of the foam. Anionic, cationic or nonionic surfactants or surfactant mixtures which are compatible with one another may be used. Low-molecular-weight or polymeric surfactants may be used, combinations of different types or of the same types of surfactants having been proved to be advantageous. Nonionic surfactants are, for example, addition products of alkylene oxides, in particular ethylene oxide, propylene oxide and/or butylene oxide, to alcohols, amines, phenols, naphthols or carboxylic acids. Advantageously, surfactants used are addition products of ethylene oxide and/or propylene oxide to alcohols containing at least 10 carbons, the addition products containing from 3 to 200 mol of added ethylene oxide and/or propylene oxide per mole of alcohol. The addition products contain the alkylene oxide units in the form of blocks or in random distribution. Examples of nonionic surfactants are the addition products of 7 mol of ethylene oxide to 1 mol of tallow fatty alcohol, reaction products of 9 mol of ethylene oxide with 1 mol of tallow fatty alcohol and addition products of 80 mol of ethylene oxide to 1 mol of tallow fatty alcohol. Other commercial nonionic surfactants comprise reaction products of oxo alcohols or Ziegler alcohols having 5 to 12 mol of ethylene oxide per mole of alcohol, in particular having 7 mol of ethylene oxide. Other commercial nonionic surfactants are obtained by ethoxylation of castor oil. 12 to 80 mol, for example, of ethylene oxide are attached per mole of castor oil. Other commercial products are, for example, the reaction products of 18 mol of ethylene oxide with 1 mol of tallow fatty alcohol, the addition products of 10 mol of ethylene oxide to 1 mol of a $C_{13}/C_{15}$-oxo alcohol, or the reaction products of 7 to 8 mol of ethylene oxide to 1 mol of a $C_{13}/C_{15}$-oxo alcohol. Other suitable nonionic surfactants are phenol alkoxylates, such as p-tert-butylphenol, which is reacted with 9 mol of ethylene oxide, or methyl ethers of reaction products of 1 mol of a $C_{12}$–$C_{18}$-alcohol and 7.5 mol of ethylene oxide.

The above described nonionic surfactants can be converted, for example by esterification with sulfuric acid, into the corresponding half-esters of sulfuric acid. The half-esters of sulfuric acid are used as anionic surfactants in the form of the alkali metal salts or ammonium salts. Examples of anionic surfactants which are suitable are alkali metal or ammonium salts of half-esters of sulfuric acid of addition products of ethylene oxide and/or propylene oxide to fatty alcohols, alkali metal or ammonium salts of alkylbenzenesulfonic acid or of alkylphenol ether sulfates. Products of said type are commercially available. For example, the sodium salt of a sulfuric acid half-ester of a $C_{13}/C_{15}$-oxo alcohol reacted with 106 mol of ethylene oxide, the triethanolamine salt of dodecylbenzenesulfonic acid, the sodium salt of alkylphenol ether sulfates and the sodium salt of the sulfuric acid half-ester of a reaction product of 106 mol of ethylene oxide with 1 mol of tallow fatty alcohol are commercial anionic surfactants. Other suitable anionic surfactants are sulfuric acid half-esters of $C_{13}/C_{15}$-oxo alcohols, paraffinsulfonic acids such as $C_{15}$-alkylsulfonate, alkyl-substituted benzenesulfonic acids and alkyl-substituted naphthalenesulfonic acids such as dodecylbenzenesulfonic acid and di-n-butylnaphthalenesulfonic acid, and fatty alcohol phosphates such as $C_{15}/C_{18}$-fatty alcohol phosphate. The polymerizable aqueous mixture can comprise combinations of a nonionic surfactant and an anionic surfactant or combinations of nonionic surfactants or combinations of anionic surfactants. Cationic surfactants are also suitable. Examples of these are the dimethyl sulfate-quaternized reaction products of 6.5 mol of ethylene oxide with 1 mol of oleylamine, distearyldimethylammonium chloride, lauryltrimethylammonium chloride, cetylpyridinium bromide and dimethyl sulfate-quaternized stearic ester of triethanolamine, which is preferably used as cationic surfactant.

The surfactant content of the polymerizable aqueous mixture is from 0.1 to 20, preferably from 0.5 to 10% by weight. In most cases, the polymerizable aqueous mixtures have a surfactant content of from 1.5 to 6% by weight.

The polymerizable aqueous mixtures may include as component (f) at least one solubilizer. For the purposes of the invention these are water-miscible organic solvents, eg. alcohols, glycols, polyethylene glycols and monoethers derived therefrom, in which case the monoether molecules do not contain double bonds. Suitable ethers are methyl glycol, butyl glycol, butyl diglycol, methyl diglycol, butyl triglycol, 3-ethoxy-1-propanol and glycerol monomethyl ether.

The polymerizable aqueous mixtures comprise from 0 to 50% by weight of one or more solubilizers. If solubilizers are used, their content in the polymerizable aqueous mixture is preferably up to 25% by weight.

The polymerizable aqueous mixture may contain thickeners, foam stabilizers, polymerization regulators, fillers and cell nucleating agents. Thickeners are used, for example, for optimizing the foam structure and for improving the foam stability, so that the foam shrinks only slightly during the polymerization. Suitable thickeners are all natural and synthetic polymers known for this purpose which greatly increase the viscosity of an aqueous system. These can be water-swellable or water-soluble synthetic and natural polymers. Suitable thickeners are also pulverulent superabsorbents. An extensive overview of thickeners is found, for example, in the publications by R. Y. Lochhead and W. R. Fron, Cosmetics & Toiletries, 108, 95–135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Suitable water-swellable or water-soluble synthetic polymers suitable as thickeners are, for example, high-molecular weight polymers of the monoethylenically unsaturated monomers containing acid groups described under (a), for example high-molecular-weight homopolymers of acrylic acid and/or methacrylic acid or slightly crosslinked copolymers of acrylic acid and/or methacrylic acid and a compound which contains at least two ethylenically unsaturated double bonds, eg. butanediol diacrylate. Compounds which are also suitable are high-molecular weight polymers of acrylamide and methacrylamide or copolymers of acrylic acid and acrylamide having molar masses of more than one million. Copolymers of this type are known as thickeners. Known thickeners are also high-molecular-weight polyethylene glycols or copolymers of ethylene glycol and propylene glycol and high-molecular-weight polysaccharides such as starch, guar seed meal, carab bean meal or derivatives of natural substances such as carboxymethylcellulose, hydroxyethylcellulose, hydroxymethylcellulose, hydroxypropylcellulose and cellulose mixed ethers. A further group of thickeners are water-insoluble products, such as finely divided silicon dioxide, pyrogenic silicic acids, precipitated salicic acids in hydrophilic or hydrophobic forms, zeolites, titanium dioxide, cellulose powders or other finely divided powders of crosslinked polymers different from superabsorbers. Polymerizable aqueous mixtures can comprise the thickeners in amounts of up to 30% by weight. When thickeners of this type are used, they are present in an amount of from 0.1, preferably from 0.5 to 20, % by weight in the polymerizable aqueous mixture.

To optimize the foam structure, hydrocarbons having at least 5 carbons in the molecule may be added to the aqueous reaction mixture. Examples of suitable hydrocarbons are pentane, hexane, cyclohexane, heptane, octane, isooctane, decane and dodecane. Suitable aliphatic hydrocarbons can be straight-chain, branched or cyclic and have a boiling point above the temperature of the aqueous mixture during foaming. The aliphatic hydrocarbons prolong the life of the as yet unpolymerized foamed aqueous reaction mixture. This facilitates the handling of the unpolymerized foams and enhances the process reliability. The hydrocarbons are used in amounts of from 0 to 10% by weight, based on the polymerizable aqueous mixture. When used, their amounts present in the aqueous mixture are preferably from 0.1 to 5% by weight.

To vary the properties of the superabsorbents, for example the absorption rate and the absorption capacity of water, it can be advantageous to add a polymerization regulator or a mixture of a plurality of polymerization regulators to the aqueous reaction mixture. Examples of suitable regulators are formic acid, thio compounds such as 2-mercaptoethanol, mercaptopropanol, mercaptobutanol, dodecylmercaptan, thioglycolic acid or amines such as ethanolamine, diethanolamine, triethanolamine, triethylamine, morpholine or piperidine. The amounts of polymerization regulators can be up to 10% by weight, based on the monomers used. If polymerization regulators are used, they are preferably employed at from 0.1 to 5% by weight, based on the monomers.

The constituents specified under (g) which may be present or absent, if employed can be used individually or in a mixture in the preparation of the polymers according to the invention. However, the procedure can be carried out in the absence of thickeners, foam stabilizers, fillers, cell nucleating agents and polymerization regulators.

In the preparation according to the invention of water-absorbent foamed crosslinked polymers, the above described polymerizable aqueous mixture is foamed in a first process step. For this purpose, a gas which is inert to free-radicals is dispersed in the aqueous monomer phase in the form of fine bubbles so that a foam forms. The gas bubbles are introduced using, for example, beating, shaping, stirring or whipping apparatus. In addition, it is possible to produce foams of this type by gases exiting from a liquid-covered orifice or by exploiting turbulence phenomena in flows. Finally, forming lamellae on wires or screens can be utilized for this purpose. These diverse methods may if appropriate be combined with one another. Examples of suitable gases inert to free radicals are nitrogen, carbon dioxide, helium, neon and argon. Preferably, nitrogen is used.

Foaming and polymerization are preferably performed separately. The polymerizable aqueous mixture can be foamed, for example, in industrial equipment which is known for producing urea/formaldehyde foams, cf. Frisch and Saunders, Polymeric Foams Part II, (1973) 679 ff. In the laboratory, the polymerizable aqueous mixture can be foamed most simply with a conventional kitchen appliance which is fitted with egg whisks. The whipped foam is preferably produced in an inert gas atmosphere. Examples of inert gases which can be used are nitrogen, noble gases or carbon dioxide. To produce the foam, all components of the reaction mixture are combined, expediently, all water-soluble components first being dissolved in water and only then are the water-insoluble substances added. Depending on which whipped foam production process is used and on the initiator present in the polymerizable aqueous mixture, it can also be advantageous not to add the initiator to the mixture until the end of the whipping process. The consistency of the whipped foams can be varied within a broad range. It is thus possible to produce light flowing whipped foams or else stiff sliceable foams. The mean size of the gas bubbles, their size distribution and their arrangement in the liquid matrix can likewise be varied in a broad range by the choice of surfactants, the solubilizers, thickeners and foam stabilizers, cell nucleating agents, temperature and whipping technique, so that the density, open-cell character or wall thickness of the matrix material can be set in a simple manner. The temperatures of the polymerizable aqueous mixture during the foaming operation are in the range from −10 to 100, preferably from 0 to +50° C. Foam production temperatures are always employed which are below the boiling point of constituents of the polymerizable aqueous mixture. The foam can also be produced under elevated pressure, eg. at from 1.5 to 25 bar. However, atmospheric pressure is preferably employed.

The particularly preferred foam is described in the applicant's German Patent Application P 195 409 51.5, the contents of which are herein incorporated to complete extent by reference.

The composite materials can be produced in two different ways:

a) The foam elements are produced directly on the support.

Expediently, the monomer foam, which may have been whipped, is applied to the support material in the desired grid pattern and at a thickness of from 0.05 to 20 mm, preferably from 0.1 to 10 mm, and then polymerized to completion. It is possible to apply the foam elements using all customary methods, e.g. using stencils, using printing techniques such as screen-printing methods or by specific spraying-on of individual foam elements, e.g. using the ink-jet method. The free-standing foam elements thus obtained can then be polymerized in a suitable manner, as described in the abovementioned patents and patent applications. The preferred foams are polymerized as described in P 195 40 951.5. Depending on the initiator used, it can be performed by temperature elevation, by the action of light, by irradiation with electron beams or by temperature elevation and the action of light. To increase the temperature of the foamed polymerizable aqueous mixture, all processes customary in industry may be employed, for example the foam can be brought into contact with heatable plates, the action of infrared irradiation on the polymerizable foam or heating using microwaves.

If thicker layers of a foam are to be produced, e.g. foams having thicknesses of several centimeters, heating the polymerizable foamed material using a microwave is particularly advantageous, because relatively uniform heating can be achieved in this manner.

The polymerization is performed, for example, at from 20 to 180, preferably in the range from 20 to 100, ° C.

When polymerization is initiated by the action of light on the foamed polymerizable material, all conventional sources of illumination can be employed, if their emission spectrum is adapted to the photoinitiator used. When the polymerization is started by illumination, a combination of a photoinitiator with a thermal initiator is advantageously used, or else a photoinitiator is advantageously used which can also act as a thermal initiator, eg. azo initiators. Since the foam heats greatly during the polymerization owing to the high heat of polymerization, this achieves in this manner a particularly faster and more effective polymerization reaction course. When polymerization is initiated by the action of light, the polymerization temperature is in the range from 0 to 150, preferably from 10 to 100, ° C.

An essential advantage of the process of the invention is that the polymerization proceeds with substantial retention of the structure of the foamed polymerizable aqueous mixture, ie. the polymerizable foam changes only insignificantly in volume during the polymerization. The polymerization reaction is influenced by the starting temperature, the initiation method or the heat removal. The polymerization temperature is preferably controlled to prevent boiling of the polymerizable aqueous mixture. As polymerization proceeds, solidification of the foam occurs owing to increasing gel formation. After polymerization is complete, a foamed hydrogel is present which contains from 30 to 80% by weight of water. The foam, at least in part, has an open-cell structure. For the use of the foam as a superabsorbent, a residual moisture content of from 1 to 45, preferably from 15 to 35, % by weight is desirable. The foamed hydrogel produced in the polymerization is therefore usually dried. To obtain a flexible foam, it must have a certain residual moisture content. The water content is highly dependent on the density of the foam produced. The higher the density, the greater the residual moisture which must be set. Therefore, an upper limit of from 35 to 45% by weight of water can be highly expedient. If a batch having a very high solids content is polymerized giving a foam having a very high density, it may even be necessary to further moisten the foam after the polymerization in order to obtain the necessary flexibility.

The foam can be dried using all conventional methods, for example by heating with a hot gas stream, by applying vacuum, by infrared irradiation, or by microwave heating, which last method again proves advantageous here in the drying of large-volume shaped bodies.

As an alternative to the above procedure, in the case of relatively thin whipped foams, the foam can be applied using a stencil and the stencil left on the support material until after the polymerization.

b) The foam elements are applied in the finished state

The structural elements can be produced separately and then fixed to the support material, e.g. by glueing, at individual points or over the complete surface. It is essential that the foam shows good adhesion to the support, since only then can delamination of the foam elements from the support be prevented. In the event of delamination, the desired effect would not occur, since the foam elements would then swell unhindered in a three-dimensional manner.

To achieve good adhesion it is advantageous to apply the monomer foam to the support and then to polymerize it. With many substrates, e.g. polypropylene or polyester webs made hydrophilic, or foams, very good adhesion is achieved per se, without an additional adhesive or glue being necessary. However, it can be advantageous in the case of individual substrates, in particular in the case of smooth films or foils, to use an adhesive or to bind the foam to the support physically. The method which is chosen or the type of adhesive which shows optimum effect is directly dependent on the support material used.

In the above-described process, a predominantly or at least partially open-cell superabsorbent foam is obtained which is relatively hard and brittle in the completely dried state. However, for many applications foams and foam elements are demanded which are the relatively hard and brittle foam initially obtained can be made flexible. This can be achieved using external plasticizers or by internal flexibilization.

External plasticizers are components which, in addition to the gel-forming components, are either added to the reaction mixture prior to foaming, or are applied to the foam afterwards. Examples of plasticizers which are used are hydrophilic and hygroscopic substances. External flexibilization is primarily achieved by the specific setting of a defined residual water content. In addition, the flexibilization can be improved by the use of, for example, polyols such as glycerol, poly(alkylene glycols) such as poly(ethylene glycols) or poly(propylene glycols), or cationic surfactants. Examples of suitable cationic surfactants are dimethylsulfate-quaternized reaction products of 1 mol of oleylamine with 5 to 10 mol of ethylene oxide, distearyldimethylammonium chloride, lauryltrimethylammonium chloride, cetylpyridinium bromide and ethanolamine esters of long-chain fatty acids such as diethanolamine stearate, ethanolamine stearate and triethanolamine stearate, which is preferably used as external plasticizer.

Internal flexibilization of the foam includes the use of plasticizing components which are incorporated into the gel structure. These components may be substances which themselves bear unsaturated groups and are present in the polymerizable aqueous mixture as monomer (b) in the polymerization and are conjointly incorporated into the gel structure, or they react with the gel-forming material. The internal plasticizer is intended to decrease the glass temperature of the polymer comprising the superabsorbent. Examples of internal plasticizers are olefins, esters of ethylenically unsaturated $C_3$–$C_5$-carboxylic acids and monohydric $C_2$–$C_{30}$-alcohols or poly(ethylene glycol) monoesters or poly(propylene glycol) monoesters of monoethylenically unsaturated $C_3$–$C_5$-carboxylic acids. For internal flexibilization, monomers (b) are suitable which decrease the glass temperature of the copolymers formed with the monomers (a), eg. vinyl esters of saturated carboxylic acids containing at least 4 carbons, alkyl vinyl ethers having at least 2 carbons in the alkyl, vinyllactams and alkyl-substituted styrenes such as ethylstyrene.

As has already been disclosed above, an inhomogeneous density of crosslinking can be produced in the novel superabsorbent foams even during their production. This is particularly advantageous if use is made as monomers of the above described components (a) acrylic acid, methacrylic acid, vinylsulfonic acid, acrylamidopropanesulfonic acid or their mixtures and
(c) a mixture of at least one water-soluble and at least one water-insoluble crosslinker.

Nevertheless, it can be desirable to modify the degree of crosslinking of the foam later. In order to achieve this aim, for example, latent crosslinking sites can be incorporated into the gel during polymerization by adding suitable monomers which do not lead to crosslinking reactions under the conditions of foam production, but, under specific conditions which can be employed later, eg. as a result of greatly elevated temperature, are able to form further crosslinking points in the gel structure. An example of the use of monomers of this type is the incorporation of hydroxyl-containing compounds which, at elevated temperature, ie. above 150° C., are able to react with the carboxyls in the foam structure. Examples of suitable compounds which have latent crosslinking sites are hydroxyethyl acrylate, hydroxypropyl acrylate, hydroxybutyl acrylate, monoacrylic esters of glycerol, monoacrylates or monomethacrylates of poly(ethylene glycols) containing at least 2 ethylene glycol units, monoacrylates or monomethacrylates of poly(propylene glycols) containing at least 2 propylene glycol units and monomethacrylates of polyhydric alcohols, eg. hydroxybutyl methacrylate, hydroxypropyl methacrylate, hydroxyethyl methacrylate or glycerol monomethacrylate.

A further potential method for homogeneous post-crosslinking is the subsequent addition of crosslinking reagents, ie. compounds having at least two reactive groups which, under suitable conditions, eg. on heating to above 70° C., are able to react with the acid groups of the foamed hydrogel. In this case it is also possible to modify the inhomogeneous density of crosslinking, under the control of the depth penetration of the crosslinker. Suitable crosslinkers form covalent or ionic bonds with the polymer matrix carboxyls; they are compounds which have at least two functional groups of identical or different types, eg. hydroxyl, amino, quaternary ammonium, isocyanato, epoxy, aziridino, ester or amide. Preferred crosslinkers are polyhydric alcohols such as glycerol or bisepoxides. The crosslinkers may be applied to the foamed material by spraying, dipping or gas-phase precipitation, for example.

The novel absorber elements can be employed in all types of hygiene or sanitary articles or in wound dressings, for example baby diapers, sanitary towels or incontinence products. Articles of this type are formed in a conventional manner, for example as described in WO-A-94/22502. The absorber elements can be used instead of the superabsorbent foam layers described in this publication.

The invention is described in more detail below with reference to FIGS. 1 to 4 and the examples, without being restricted thereto.

In the figures:

FIG. 2 shows a diagrammatic cross-section through the absorber element of FIG. 1 before and after swelling;

FIG. 3 shows a diagrammatic cross-section through an absorber element of two composite materials before swelling;

Figure 1:
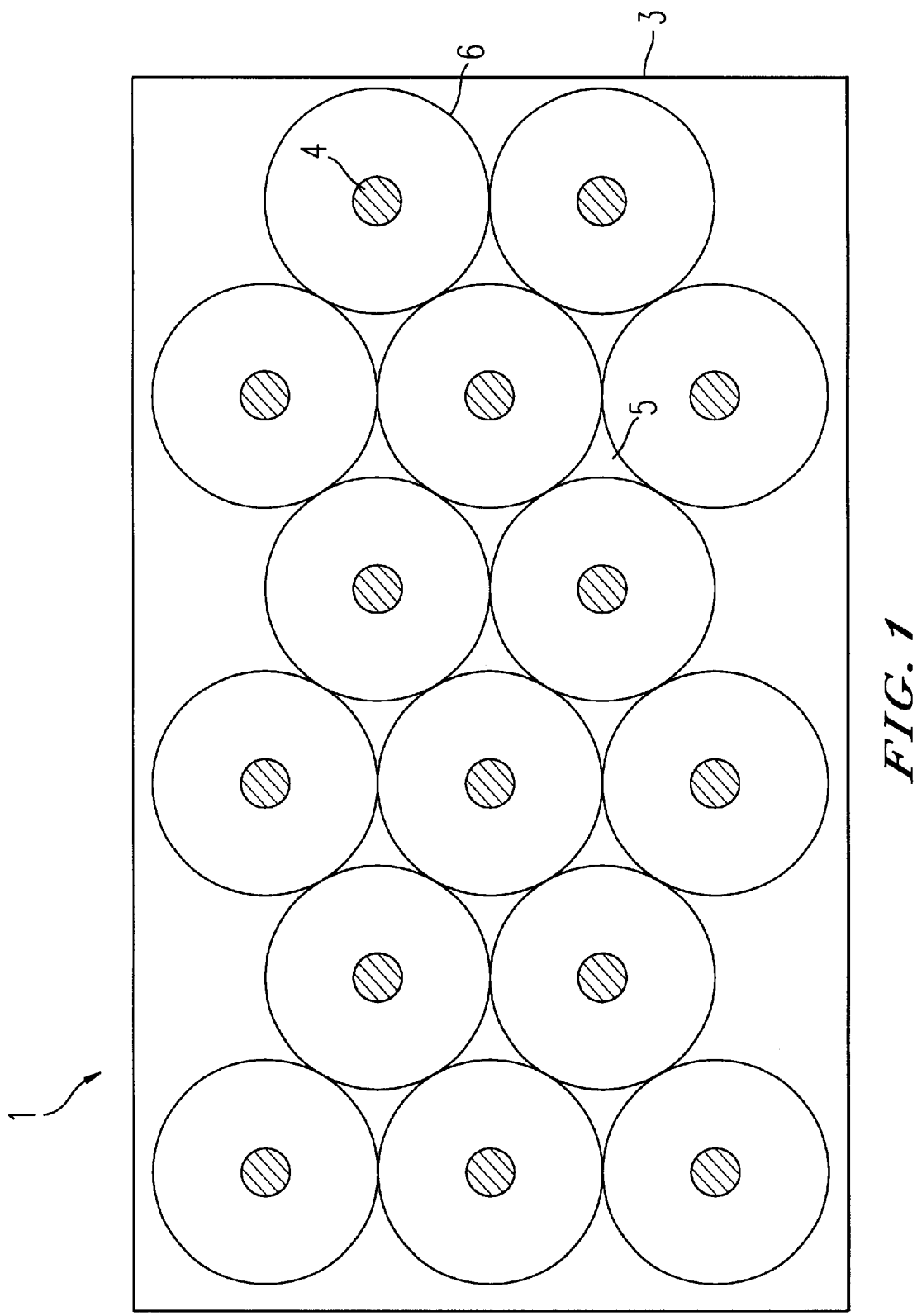
FIG. 1 shows a diagrammatic view of an absorber element of a composite material before and after swelling.

FIG. 1 shows an absorber element of a composite material 1 made of a support web 3 on which are applied a plurality of foam elements 4 which are in the shape of cylinders. When they absorb liquid, the foam elements 4 swell, i.e. the swollen foam elements 6 having substantially greater cross-section are obtained. The distance between the foam elements 4 is chosen in such a manner that they touch after swelling, as can be seen from FIGS. 1 and 2. Between the swollen foam elements 6 there remain gaps 5 which ensure high vertical permeability for the liquid to be absorbed. FIG. 2 shows that the foam elements 4 can expand to only a restricted extent near the support surface, whereas they can expand to an increasingly unrestricted extent as the distance from the support increases, so that the swollen foam elements 6 have the conical structure shown in FIG. 2. Thus, the composite material 1 or the absorber element can expand in only one direction, that is perpendicularly to the surface of the support 3.

FIG. 3 shows an absorber element made of two composite materials 1 and 2. Foam elements 4 of the type shown in FIGS. 1 and 2 are applied to each support 3, which can be of different natures. The two composite materials are combined with one another in a manner such that the foam elements 4 of the one composite material 1 penetrate into the spaces between the foam elements 4 of the other composite material 2. The resulting absorber element has the advantage that the absorption capacity for liquids is roughly doubled in this manner.

Figure 4:
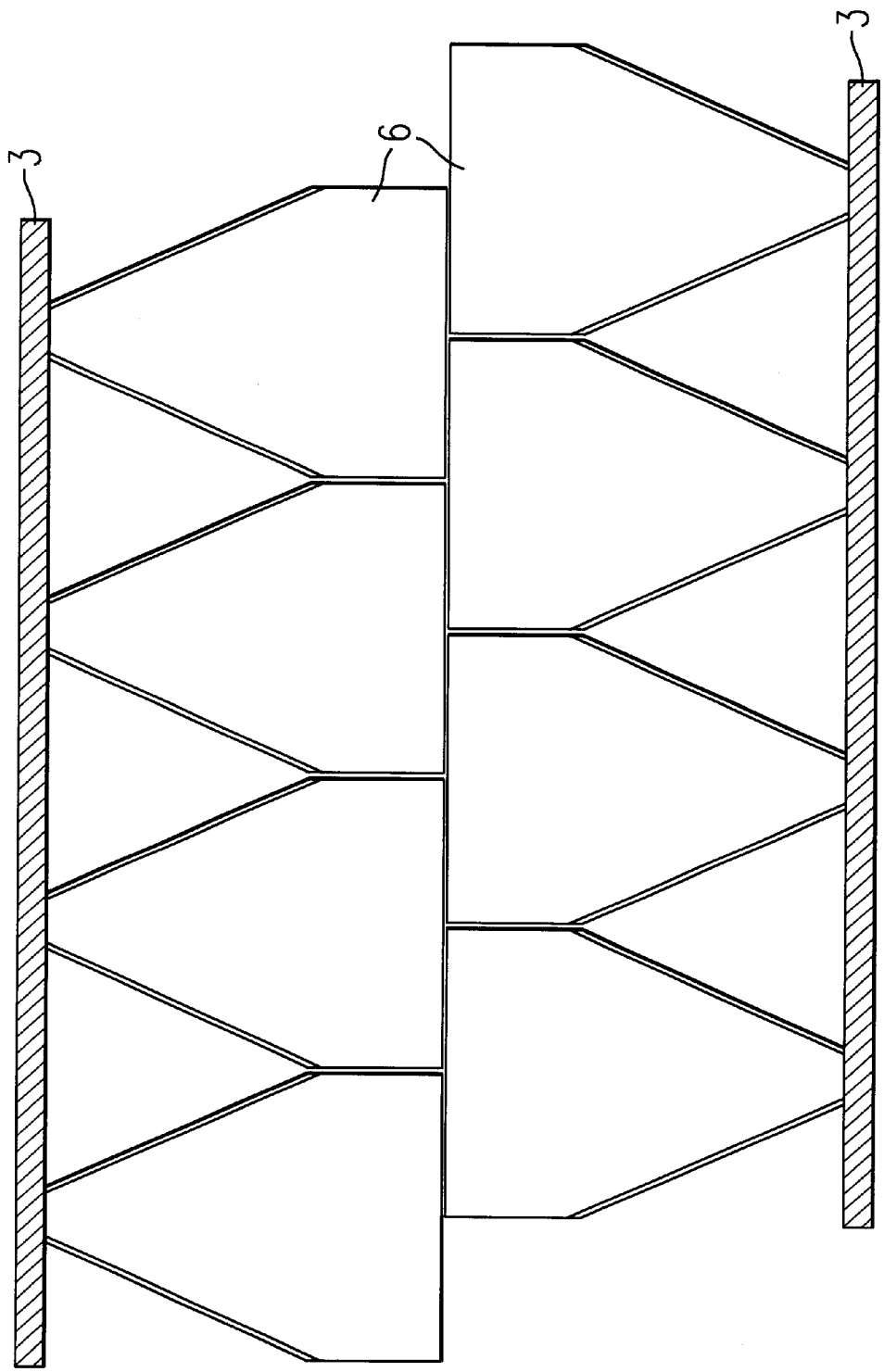
FIG. 4 shows a diagrammatic cross-section through the absorber element of FIG. 3 after swelling.

FIG. 4 shows the absorber element of FIG. 3 after swelling. It can be seen that it has expanded only perpendicularly to the support surface, and the shape of the swollen foam elements 6 is as shown in FIG. 2. The foam elements force the two composite materials apart perpendicularly to the support surface, so that the foam elements slide out from the gaps into which they penetrate and the composite materials thus move apart from one another.

The studies described in the examples below are carried out as follows:

To determine the contents extractable from the foamed superabsorbent, a dried and ground foam sample is dispersed in a 0.9% strength by weight sodium chloride solution and the dispersion is stirred for 1 hour. The foamed material is then filtered off and the amount of extractable content in the filtrate determined by titrimetry.

The absorption capacity of the composite material for water per gram of material is determined on sample pieces, each of which weigh 1 g. Retention is studied in this case by the teabag test. The liquid used in the test is a 0.9% strength sodium chloride solution. 1 g of the material is placed in a teabag which is then sealed, care being taken to ensure that the teabag leaves sufficient space for complete swelling. The teabag is then immersed in the liquid for a defined time and after draining for 10 minutes is reweighed. For calculation of the absorption capacity, a blank test must be carried out in which a teabag without material is immersed in the solution and the weight of the teabag is determined after the above specified draining time of 10 minutes. The absorption capacity is then given by the following relationship $$\text{Absorption capacity} = \frac{\text{Weight of teabag containing sample} - \text{weight of teabag in blank test}}{\text{Initial weight of sample}}$$

The retention is determined as follows:

The same procedure is followed as above, but instead of draining, the teabag is centrifuged for 3 min at an acceleration of 250 g.

$$\text{Retention} = \frac{\text{Weight of teabag after centrifuging} - \text{weight of teabag in blank test}}{\text{Initial weight of sample}}$$

The absorption speed (AS below) was determined by cutting 1-g rectangular samples from composite material or absorber element using a sharp knife, pouring 20 g of synthetic urine over the samples in a Petri dish, and measuring with a stopwatch the time required for the sample to absorb the synthetic urine completely. The absorption speed (AS) in g/g. sec is calculated from:

$$AS = 20 \text{ g}/[1 \text{ g·time measured (in sec)}]$$

Synthetic urine formula:
the following salts are dissolved in 1 l of distilled water:
2.00 g of KCl
2.00 g of $Na_2SO_4$
0.85 g of $NH_4H_2PO_4$
0.15 g of $(NH_4)_2HPO_4$
0.19 g of $CaCl_2$
0.23 g of $MgCl_2$
The salts used must be anhydrous.

EXAMPLE 1

The following components were mixed in a glass beaker using a magnetic stirrer:

224.23 g of a 37.3% strength sodium acrylate solution in water
49.68 g of water
21.36 g of acrylic acid
3.15 g of the product of adding 80 mol of ethylene oxide to 1 mol of tallow fatty alcohol
2.60 g of pentane
1.05 g of the triacrylic ester of glycerol etherified with 20 mol of ethylene oxide
0.53 g of 1,4-butanediol diacrylate.

The resulting homogeneous mixture was placed in a 2 l flask, into which argon was introduced from the bottom. Two egg whisks, each of which was connected to a type RW 20 DZM Janke & Kunkel stirrer, were inserted into the flask. The argon stream was set so that it bubbled through the reaction mixture at a rate of 80 l/h. The two stirrers were initially set to a speed of 60 rpm. 45.00 g of finely ground commercial superabsorbent based on slightly crosslinked poly(sodium acrylate) (particle size <100 μm) were added to the reaction mixture and mixed in homo-generously. The flask opening was virtually completely sealed with parafilm and the stirrer speed was set to 1000 rpm. The mixture was whipped at this speed for 20 min. 5 minutes before whipping ended, 11.9 g of a 3% strength aqueous solution of 2,2'-azobis-(2-amidinopropane) dihydrochloride were added to the flask. After the whipping period ended, a fine-celled readily flowable whipped foam was obtained.

A thermobonded polypropylene web (thickness: 0.19 mm, 20 g/m$^2$) which had been rendered hydrophilic was first placed into a teflon-coated aluminum mold (width: 10 cm, length 20 cm), and a 1.5 mm-thick teflon stencil was placed on this. The stencil contained 5 mm bore holes with a distance of 5 mm between the bore holes, corresponding to the pattern sketched in FIG. 1. The foam produced as above was spread into the openings using a rubber scraper. The mold was then heated on a conventional hot plate (Ceran 500) at 163° C. for 2 min. The sample was then irradiated for 2 min using a UV lamp (UVASpot 400, from Hönle), while the heating was continued, and finally, the sample was heated for a further 2 min without irradiation.

The composite obtained after taking off the stencil was completely dried in a vacuum drying cabinet at 70° C. A portion of the sample was ground for analytical purposes, while the remainder was adjusted to a residual moisture content of 25% using distilled water.

The polymerized foam elements adhered very well to the support web.

Properties of the composite material obtained:

| | |
|---|---|
| Swelling behavior: | The superabsorber points swelled uniformly, with retention of the composite |
| Absorption: | 23.0 g/g |
| Retention: | 10.2 g/g |
| Extractables: | 9.8 % |
| AS: | 0.5 g/g sec |

EXAMPLE 2

The procedure was identical to that of Example 1, but the stencil used was a 3 mm-thick teflon stencil containing 8 mm bore holes with a spacing between the bore holes of 11 mm.

The polymerized foam elements adhered very well to the support web.

Properties of the composite material obtained:

| | |
|---|---|
| Swelling behavior: | The superabsorber points swelled uniformly with retention of the composite |
| Absorption: | 24.10 g/g |
| | 10.8 g/g |
| Extractables: | 9.4% |
| AS: | 0.43 g/g sec |

EXAMPLE 3

Example 1 was repeated, but 55.0 g of finely ground superabsorbent as defined in Example 1 were used.

The polymerized foam elements adhered very well to the support web.

Properties of the composite material obtained:

| | |
|---|---|
| Swelling behavior: | The superabsorber points swelled uniformly with retention of the composite |
| Absorption: | 22.3 g/g |
| Retention: | 9.8 g/g |
| Extractables: | 11.5% |
| AS: | 0.48 g/g sec |

Comparison Example 1

A whipped foam according to Example 1 was produced.

A thermobonded polypropylene web (thickness 0.19 mm, 20 g/m$^2$) which had been rendered hydrophilic was then placed into a teflon-coated aluminum mold (width: 10 cm, length 20 cm) having a 3 mm-high rim. The above whipped foam was spread on this web in a thickness of 3 mm. The mold was heated on a conventional hot plate (Ceran 500) at 163° C. for 2 min, then the sample was irradiated for 2 min with a UV lamp (UVASpot 400, from Hönle), while the heating was continued, and, finally, the sample was heated for a further 2 min without irradiation.

The composite obtained, which adhered together very well, was completely dried at 70° C. in a vacuum drying cabinet. A portion of the sample was ground for analytical purposes, while the remainder was adjusted to a residual moisture content of 25% using distilled water.

Swelling behavior: On swelling in an excess of synthetic urine, the partially swollen foam layer tore. The majority detached completely from the support, while a smaller proportion remained on the support in the form of a thin layer. The detached foam layer swelled isotropically.

Comparison Example 2

The whipped foam was produced identically with Comparison Example 1. An identical web was first placed into the abovementioned mold as in Comparison Example 1. A closed foam layer of 3 mm thickness was then spread on the web and the foam layer was covered with a further web.

Polymerization was carried out as in Comparison Example 1.

A composite having components adhering together very well was obtained.

Swelling behavior: On swelling in an excess of synthetic urine, the composite tore into three parts. The partially swollen foam layer detached for the most part from both webs, while a smaller portion remained on the two supports in the form of thin layers. The detached foam layers swelled isotropically.

Comparison Example 3

The whipped foam was produced identically with Comparison Example 1. A 1.5 mm-high whipped foam layer was then placed into the above-described mold and the web was then placed in the mold, onto which a further 1.5 mm-high whipped foam layer was spread. The subsequent procedure was again identical to Comparison Example 1.

A composite was again obtained having components which adhered to one another very well.

Swelling behavior: On swelling in an excess of synthetic urine, the composite tore into three pieces. The partially swollen foam layers for the most part detached from the web on both sides, while a small portion remained on both sides of the support in the form of thin layers. The detached foam layers swelled isotropically.

EXAMPLE 4

A composite material as described in Example 1 was produced.

An absorber element having a thickness of 2 mm was produced from two of the composite materials obtained by simply pushing one into the other in the manner described above. On swelling in an excess of 0.9% strength salt solution, or synthetic urine, the two interlinked composites separated. The thickness of the absorber element increased from 2 mm to 5.5 mm.

Properties of the absorber element:

| Absorption: | 1.96 g/cm$^2$ |
| --- | --- |
| Retention: | 0.86 g/cm$^2$ |
| AS: | 0.50 g/g sec |

The absorption capacity per unit area approximately doubled in comparison with the single composite without a significant loss in absorption speed.

EXAMPLE 5

The procedure was identical with Example 4, except the stencil used was a teflon disc whose bore holes did not have perpendicular walls, but walls inclined at 75°.

The polymerized foam elements adhered very well to the support web.

Properties of the composite material obtained:

| swelling behavior: | The superabsorber points swelled uniformly with retention of the composite |
| --- | --- |
| Absorbtion: | 22.1 g/g, equivalent to 0.88 g/cm$^2$ |
| Retention: | 9.8 g/g, equivalent to 0.39 g/cm$^2$ |
| Extractables: | 9.4% |
| AS: | 0.43 g/g sec |

An absorber element having a thickness of 1.9 mm was produced from two of the composites obtained by simply pushing one into the other in the above-described manner. On swelling in an excess of 0.9% strength salt solution or synthetic urine, the two interlinked composites moved apart from one another, as shown in FIG. 4. The thickness of the absorber element increased from 1.9 mm to 5.2.

Properties of the absorber element:

| Absorption: | 1.64 g/cm$^2$ |
| --- | --- |
| Retention: | 0.74 g/cm$^2$ |
| AS: | 0.45 g/g sec |

The absorption capacity per unit area approximately doubled without a loss in absorption speed.

We claim:

1. An absorber element of at least one composite material having absorbent elements on a support in which a plurality of elements (4) of a superabsorbent foam are arranged on at least one support (3) in a grid pattern at distances so that the elements (4) in the swollen state touch at their peripheries away from the support but expand to only a limited extent near the support, the absorber elements being obtained by
    (I) foaming a polymerizable aqueous mixture which consists of
        (a) monoethylenically unsaturated monomers containing acid groups which are at least 50 mol % neutralized,
        (b) optionally with other monoethylenically unsaturated monomers,
        (c) crosslinkers,
        (d) initiators,
        (e) from 0.1 to 20% by weight of at least one surfactant,
        (f) optionally with one or more solubilizers and
        (g) optionally with thickeners, foam stabilizers, polymerization regulators, fillers and/or cell nucleating agents,
    the foaming being performed by dispersing fine bubbles of a gas inert to free radicals,
    (II) applying the foamed mixture to the support in a grid pattern, and
    (III) polymerizing the foamed mixture, forming a foamed hydrogel and optionally setting the water content of the foamed polymer to from 1 to 60% by weight.

2. An absorber element as claimed in claim 1, wherein two composite materials (1, 2) face one another with the sides bearing the elements (4) in a manner such that the elements (4) of the one composite material (1) penetrate into the spaces between the elements (4) of the other composite material (2).

3. An absorber element as claimed in claim 2, wherein, in the case of at least one composite material (1, 2), gaps (5) remain between the swollen foam elements (6).

4. An absorber element as claimed in claim 3, wherein the foam elements (4) are cylinders or cylindrical elevations or elevations having pentagonal cross section.

5. An absorber element as claimed in claim 1, wherein the swollen foam elements (6) have a closed surface.

6. An absorber element as claimed in claim 5, wherein the foam elements (4) are elevations having triangular, square, rectangular or hexagonal cross section.

7. An absorber element as claimed in claim 1, wherein the distance between two foam elements (4) is up to 20% less than the distance which is required for the swollen foam elements (6) to come into contact with one another.

8. An absorber element as claimed in claim 1, wherein the distance between two foam elements (4) is up to 50% greater than the distance which is required for the swollen foam elements (6) to come into contact with one another.

9. An absorber element as claimed in claim 1, wherein the foam elements (4) have a height of from about 1 mm to about 20 mm.

10. An absorber element as claimed in claim 1, wherein a polymerizable aqueous mixture of (a) monoethylenically unsaturated monomers containing acid groups which are at least 50 mol % neutralized, and (b) a mixture of at least one water-soluble and at least one water-insoluble crosslinker is employed.

11. An absorber element as claimed in claim 1, made with (a) acrylic acid, methacrylic acid, vinylsulfonic acid, acrylamidopropanesulfonic acid or their mixtures, and (b) a mixture of at least one water-soluble and at least one water-insoluble crosslinker.

12. An absorber element as claimed in claim 1, wherein, said water-soluble crosslinker (c) is made of acrylic and methacrylic esters of at least dihydric alcohols, or methylenebisacrylamide.

13. An absorber element as claimed in claim 1, wherein, said thickener is made of water-swellable or water-soluble synthetic or natural polymers.

14. An absorber element as claimed in claim 1, wherein, said thickener is made of pulverulent superabsorbents.

15. A hygiene or sanitary article or wound dressing comprising at least one absorber element as claimed in claim 1.

* * * * *

UNITED STATES PATENT AND TRADEMARK OFFICE
CERTIFICATE OF CORRECTION

PATENT NO. : 6,245,410 B1
DATED : June 12, 2001
INVENTOR(S) : Hans-Joachim Hähnle et al.

It is certified that error appears in the above-identified patent and that said Letters Patent is hereby corrected as shown below:

Column 17,
Line 51, "homo-generously." should read -- homogenously. --.

Column 19,
Line 62, "Rentention: 0.86 g/cm$^2$" should read -- Retention: 0.88 g/cm$^2$ --.

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,245,410 B1
DATED         : June 12, 2001
INVENTOR(S)   : Hans-Joachim Hähnle et al.

It is certified that error appears in the above-identified patent and that said Letters Patent is hereby corrected as shown below:

Column 21,
Line 22, "with one another." should read -- with one another, when in the swollen state. --.

Signed and Sealed this

Eighth Day of June, 2004

JON W. DUDAS
*Acting Director of the United States Patent and Trademark Office*